United States Patent [19]

Pariset

[11] 4,172,428
[45] Oct. 30, 1979

[54] SCAVENGEABLE FLUID FOR A FLOW PIPE OPTICAL WINDOW

[75] Inventor: Jean Pariset, Limoges, France
[73] Assignee: Sofrance S.A., France
[21] Appl. No.: 901,090
[22] Filed: Apr. 28, 1978
[30] Foreign Application Priority Data May 5, 1977 [FR] France .................... 77 13713

[51] Int. Cl.² .............................................. G01F 15/12
[52] U.S. Cl. .................................... 116/276; 350/319; 356/441
[58] Field of Search ............................ 116/117 C, 276; 350/319, 63; 356/181, 208, 73; 73/324

[56] References Cited

U.S. PATENT DOCUMENTS

| | | | |
|---|---|---|---|
| 2,111,298 | 3/1938 | Quandt et al. .................... | 116/117 C |
| 3,453,049 | 7/1969 | Wager, Jr. ........................ | 73/324 X |
| 3,861,198 | 1/1975 | Shea .................................. | 350/63 X |
| 3,861,802 | 1/1975 | Belmear, Jr. .................... | 356/181 X |
| 4,018,513 | 4/1977 | Boeke ............................... | 350/63 X |

*Primary Examiner*—Daniel M. Yasich
*Attorney, Agent, or Firm*—Gifford, Chandler, VanOphem, Sheridan & Sprinkle

[57] ABSTRACT

A device for constituting in the wall of a pipe an optical pick-up window which may be scavenged by a protective fluid. A chamber is provided with an inlet for said fluid and an outlet for said fluid, said chamber passing through said wall and opening into said pipe through an open end, the opening of which constitutes said outlet, and a tube introduced into the chamber so as to constitute in the chamber about the tube an annular conduit starting near the said inlet of the chamber and leading towards said outlet, one end of the tube being provided with said window and being placed in the chamber opposite said outlet, the other end of the tube opening outside the chamber, wherein the distance between the window and the outlet is sufficiently short for the flow of protective fluid in front of the window to be a sheet of fluid.

8 Claims, 1 Drawing Figure

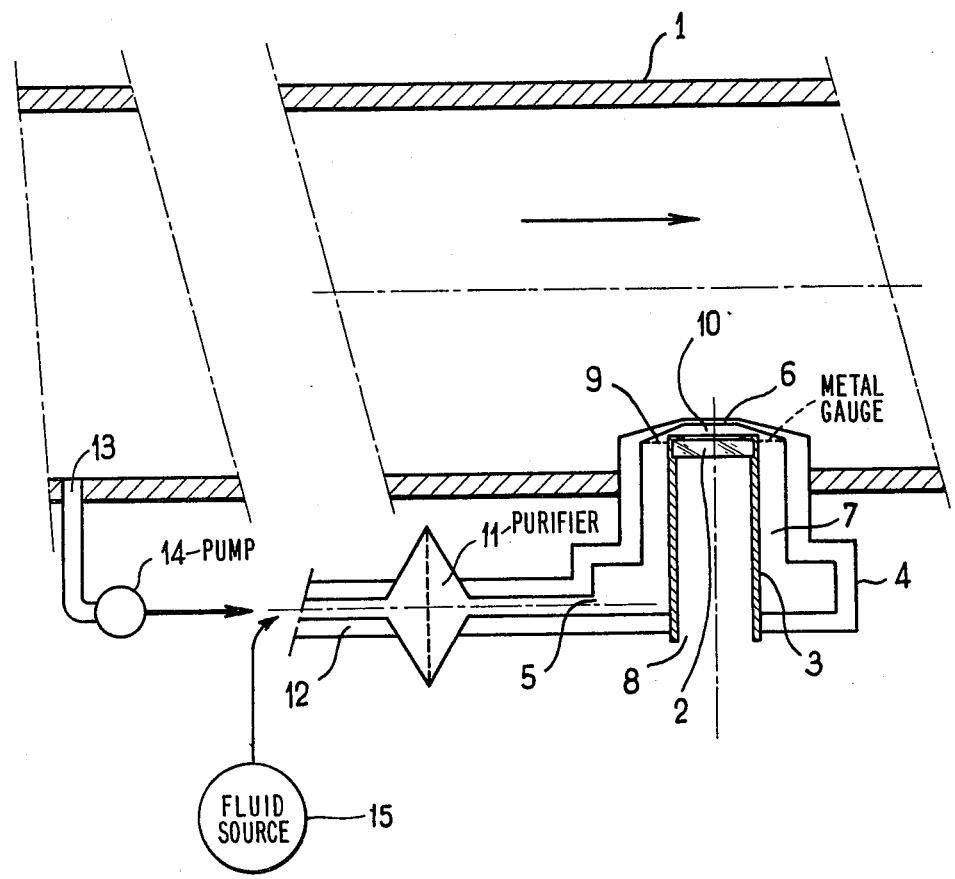

SCAVENGEABLE FLUID FOR A FLOW PIPE OPTICAL WINDOW

BACKGROUND OF THE INVENTION

I. Field of the Invention

The present invention relates to a device for constituting in the wall of a pipe an optical pick-up window which may be scavenged by a current of protective fluid.

The invention is particularly applied to the protection of the active surface of a pick-up serving to determine the degree of pollution of a fluid.

For example, it is a question of a detector for detecting hydrocarbon in water rejected into the sea, or of a pick-up for the detection of pollutant impurities in fumes.

II. Description of the Prior Art

Hydrocarbons such as gas oils, fuel oils and lubricating oils present in the bilge water in ships are separated before being rejected into the sea. The separation is not complete and a maximum threshold is fixed by the legislation in force. It is therefore necessary to monitor the water rejected. This control is made by measuring the light diffused by the micro-droplets of hydrocarbon illuminated by a beam of light.

It happens that the measurement is falsified in the long run by the deposit of hydrocarbons on the window and it has already been proposed to eliminate or substantially decelerate the formation of hydrocarbon deposit on the window by a suitable scavenging of the window by means of a fluid which is sent onto the window and then into the pipe.

In practice, eddies are frequently produced in front of the window when the scavenging fluid passes in the pipe and it is an object of the present invention to provide a device which does not produce eddies which may falsify the measurements.

SUMMARY OF THE INVENTION

The device according to the invention comprises: a chamber provided with an inlet for said fluid and an outlet therefor, said chamber passing through said wall and opening into said pipe through an open end, the opening of which constitutes said outlet; a tube introduced into the chamber so as to constitute in the chamber about the tube an annular conduit starting from near said inlet of the chamber and leading towards said outlet, one end of the tube being provided with said window and being placed in the chamber opposite said outlet, the other end of the tube opening outside the chamber, said device being characterised in that the distance between the window and the outlet is sufficiently short for the flow of protective fluid in front of the window to be a sheet of fluid only.

In a preferred embodiment, the inlet of the chamber communicates with the interior of the pipe, upstream of the outlet of the chamber with respect to the direction of flow of the pipe, via a purifier and possibly a pump.

For example, when the fluid which flows in the pipe is a mixture of fluids containing a pollutant phase and another phase in a higher proportion, fluid is continuously drawn from the mixture upstream of the window, the pollutant phase of which the deposit on the window is undesirable is continuously removed from this sample and the non-pollutant phase of the sample is continuously sent into the chamber.

A device according to the invention will be described hereinafter in the assumed case of a pick-up for detecting the presence of hydrocarbons in the bilge water discharged from a ship.

BRIEF DESCRIPTION OF THE DRAWING

The single FIGURE of the accompanying drawing is a diagram showing the device according to the invention.

DESCRIPTION OF THE PREFERRED EMBODIMENT

The mixture of fluid, in the present case a mixture of water (main phase) and of hydrocarbons (pollutant phase) flows in a pipe 1 and this mixture is analysed during flow by means of an optical pick-up typically shown by U.S. Pat. No. 3,861,198, comprising a window 2 and an apparatus associated therewith (not shown). The associated apparatus generally comprise a photocell or similar device such as a light source and light sensor shown in U.S. Pat. No. 3,861,802.

The window 2 is disposed at one end of a tubular structure 3 and it closes this end.

The tubular structure is disposed in a chamber 4 which presents a fluid inlet 5 and a fluid outlet 6, the tube 3 being placed in the chamber so as to constitute about the tube an annular space 7 accessible to the fluid introduced through the inlet 5 and constituting an annular conduit towards the fluid outlet 6 of the chamber.

The end of the tube which bears the window 2 is disposed so that said window is placed at a fraction of a millimeter from the fluid outlet 6. The other end 8 of the tube opens outside the chamber. The side wall of the tube is, of course, fluid-tight.

The annular conduit 7 is provided at its end near the window 2, with a metallic gauze 9 or other means for regularising the flow of the fluid.

The chamber 4 presents an outlet end 10 of truncated shape so as to correctly to diffuse the fluid in front of the window 2, this regular diffusion avoiding eddies at this spot and preventing introduction into the chamber through outlet 6 of the mixture flowing in pipe 1.

Upstream of the fluid inlet 5 of the chamber, the device comprises a purifier 11 in a pipe 12 which causes the inlet 5 to communicate with the inside of the pipe 1 at a spot 13 located upstream of the point in the pipe where the window 2 is located. A pump 14 is possibly used for ensuring the circulation of the sample in the pipe 12.

The circulation of the water in the branch circuit constituted by the pipe 12 and the chamber 4 ensures a continuous scavenging of the surface of the window 2 which faces the flow in the conduit 1. Due to the purification at 11, this water does not contain hydrocarbons and cannot pollute the surface of the window.

In this way, the deposits on the window are avoided or considerably retarded, this making it possible to avoid, or reduce the frequency of the dismantling operations for cleaning the window.

At the same time, the risks of damage due to the fragility of the optical system are reduced.

At the moment of calibration of the outside apparatus (optical and electronic), it is possible to stop the flow in conduit 1 and allow the detector assembly to fill with the protective liquid which constitutes a rinsing liquid. It is thus possible to verify the state of cleanliness of the window without being obliged to dismantle it.

The invention is obviously not limited to a particular nature of window. Nor is the invention limited to a particular protective fluid, although preference is given to water; the protective fluid may be drawn from a pipe, as in the example described, or it may come from a separate origin 15, as shown in the drawing figure. The shape of the chamber may vary, but preference is given to shapes of revolution; the portion of the chamber which is included between the window and the outlet of the chamber preferably has the form of a frustum of a cone of which the depth is substantially shorter than the width, as in the example shown.

What is claimed is:

1. A device for constituting in the wall of a pipe an optical pick-up window for monitoring and analyzing a fluid in a vessel, said window being scavenged by a current of protective fluid from a source of protective fluid, said device comprising:

a chamber provided with an inlet for said protective fluid, said inlet being connected to said source of protective fluid, and an outlet for said fluid, said chamber passing through said wall and opening into said pipe through an open end, the opening of which constitutes said outlet, said protective fluid entering said inlet;

a tube introduced into the chamber so as to constitute in the chamber about the tube an annular conduit starting from near said inlet of the chamber, leading towards, and ending near said outlet, one end of the tube being provided with said window and being placed in the chamber adjacent said outlet, the other end of the tube opening outside the chamber; and means for regularizing the flow of protective fluid about the end of the annular conduit near said window;

whereby the distance between the window and the end of the outlet is sufficiently short so that the flow of protective fluid in front of the window is caused to be only a sheet of fluid.

2. The device of claim 1, wherein the chamber comprises means for regularising the flow of fluid about the end of the annular conduit near the window.

3. The device of claim 2, wherein the means for regularizing the flow of fluid about the end of the annular conduit near the window comprises a metallic gauze.

4. The device of claim 1, wherein said inlet of the chamber communicates with the inside of the pipe, upstream of said outlet of the chamber with respect to the direction of flow in the pipe, by means of a purifier.

5. The device of claim 4, wherein the fluid flowing in the pipe contains a pollutant phase and a non-pollutant phase and the purifier is adapted to eliminate the pollutant phase.

6. The device of claim 1, wherein the portion of chamber included between the window and the outlet of the chamber is in the form of a frustum of a cone whose depth is substantially shorter than its width.

7. The device of claim 1, wherein said inlet of said chamber communicates with the inside of the pipe, upstream of said outlet of said chamber with respect to the direction of flow in the pipe, by means of a pump.

8. The device of claim 1, wherein the distance from the window to the outlet is a fraction of a millimeter.

* * * * *